(12) United States Patent  
Nelson et al.

(10) Patent No.: US 8,282,653 B2  
(45) Date of Patent: Oct. 9, 2012

(54) SYSTEM AND METHODS FOR CONTROLLING SURGICAL TOOL ELEMENTS

(75) Inventors: Carl Nelson, Lincoln, NE (US); Xiaoli Zhang, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 574 days.

(21) Appl. No.: 12/383,451

(22) Filed: Mar. 24, 2009

(65) Prior Publication Data

US 2009/0240259 A1    Sep. 24, 2009

Related U.S. Application Data

(60) Provisional application No. 61/070,585, filed on Mar. 24, 2008.

(51) Int. Cl.  
*A61B 19/00* (2006.01)

(52) U.S. Cl. .............. 606/130; 74/490.01; 600/417; 600/429; 700/245; 901/25; 901/26

(58) Field of Classification Search .................. None  
See application file for complete search history.

(56) References Cited

U.S. PATENT DOCUMENTS

| 4,275,986 A * | 6/1981 | Engelberger et al. ......... 414/730 |
| 2002/0082612 A1* | 6/2002 | Moll et al. .................. 606/130 |

* cited by examiner

*Primary Examiner* — Gary Jackson  
*Assistant Examiner* — Kevin Everage  
(74) *Attorney, Agent, or Firm* — Valauskas Corder LLC

(57) ABSTRACT

A light-weight, compact, highly dexterous surgical robot system for performing in vivo minimally invasive surgeries that allows precise control of position and orientation of surgical tools. The surgical robot system has three rotational degrees of freedom and one translational degree of freedom and is composed of seven links joined by three gear pairs and six turning pairs. The surgical robot system maintains an open space where a surgical tool element enters the patient to avoid self-collisions within the robot system during surgeries.

11 Claims, 4 Drawing Sheets

SYSTEM AND METHODS FOR CONTROLLING SURGICAL TOOL ELEMENTS

This application claims the benefit of U.S. Provisional Application No. 61/070,585 filed Mar. 24, 2008.

FIELD OF THE INVENTION

The present invention relates in general to surgery, and more particularly to minimally invasive surgery and an improved surgical robot system and methods for performing the same.

BACKGROUND OF THE INVENTION

Minimally invasive surgery may include various benefits such as reduced post operative discomfort, reduced chance of infection, quicker recovery times, shorter hospital stays, quicker return to full activity, smaller external scars and less internal scarring. Accurate and precise manipulation of surgical tools or instruments is desired during any surgical procedure, but this is particularly true with minimally invasive surgery.

Minimally invasive surgery, such as endoscopic procedures, is typically performed through small incisions limiting the room to maneuver the surgical tools. Although surgeries performed using minimally invasive techniques reduce patient trauma and recovery time, traditional methods of performing minimally invasive surgery also limit surgical dexterity and vision. Minimally invasive surgery is typically performed using long, rigid surgical tools that are inserted through an entry point such as a small incision or a natural orifice. For example, laparoscopy is an endoscopic procedure where surgical tools are inserted into an abdominal cavity. Therefore, the maneuverability of the surgical tools is limited due to the constraints of the entry point.

In approximately the last decade, robotic apparatuses have been applied in surgical settings to augment the surgeon's ability to manipulate surgical tools during minimally invasive surgery. Typically, robotic apparatuses include tools that are inserted into a body cavity through the entry point. Main advantages of robotic apparatuses include precise localization in terms of position and orientation of the surgical tools, reduction of surgeon hand tremor, remotely manipulated operation such as telesurgery, and limitation of risks such as the ability to constrain motion of the surgical tool within "safe regions". "Safe regions" are the areas of main focus of the surgery.

One of the primary problems with current robotic apparatuses is the voluminous size, causing competition for precious space within the operating room environment. Due to size, these apparatuses may cause unwanted safety issues by interacting with other equipment or personnel in the operating room environment. Size also has an effect on control of the robotic apparatus. Likewise, tactile feedback to enhance user-friendliness of the interface of current robotic apparatuses creates additional mass and inertia in particular parts of the apparatus, such as the robotic arms, thereby limiting effectiveness.

A key feature of most robotic apparatuses is the Remote Center of Motion ("RCM"), which allows the surgical tool to pivot about a fixed point in space usually coincident with the entry point of the tool through the entry point. Although some robotic apparatuses use a passive RCM, a mechanically constrained RCM is often considered safer. Yet some apparatuses use software to create a virtually constrained RCM.

There are a variety of ways to achieve a mechanically constrained RCM such as using a special type of wrist mechanism such as spherical wrist mechanism. For example, all rotation axes of a spherical wrist mechanism consist of revolute joints intersecting at the center of the device. One way to implement this is using parallelogram linkages, although other linkage configurations also exist.

Research has led to robotic apparatuses with spherical wrist mechanisms for specific minimally invasive surgery applications, for example, a Light Endoscope Robot ("LER") for positioning an endoscopic camera. A disadvantage of the LER, however, is that it only provides three Degrees of Freedom ("DOF")—two rotations around the entry point and one translation along an axis—due to the configuration of the spherical wrist mechanism. Yet another apparatus, similar to LER, is a force controlled robot known as $MC^2E$ with four DOF. Other known apparatuses utilize spherical wrist mechanisms with only two DOF—two rotations around the entry point. These spherical wrist mechanisms include actuators that are directly mounted at the joints, which may add inertial loads adversely affecting performance.

To enhance assimilation of surgical robot apparatuses in the operating room environment, it is desirable to have a light-weight system with a structure smaller than existing apparatuses while maintaining large orientation capabilities and precision for controlling surgical tools during minimally invasive surgery. The present invention satisfies this demand.

SUMMARY OF THE INVENTION

While the following discussion pertains to minimally invasive surgery known as laparoscopy, it is equally applicable to any form of endoscopic procedures such as arthroscopy, thoracoscopy, mediastinoscopy, cystoscopy, hysteroscopy, colposcopy, fetoscopy, and cholecystectomy to name a few.

The present invention is a light-weight, compact surgical robot system for controlling the position and orientation of surgical tool elements during minimally invasive surgery. The surgical robot system has four Degrees of Freedom ("DOF")—three rotations and one translation. All motion axes meet at a single point such that the motion of the surgical tool element is constrained to always pass through a fixed point in space—the Remote Center of Motion ("RCM"). Thus, the rotation center of the surgical robot system is located at the intersection of the three axes.

The surgical robot system according to the present invention is composed of seven links joined by three gear pairs and six turning pairs. The turning pairs are arranged such that an open space is maintained at the center of the surgical robot system—where the surgical tool element enters the patient—to avoid self-collisions within the robot system during surgeries. This is accomplished by setting the link angles between turning pairs at values no more than 90°. The minimally invasive surgery entry point coincides with the rotation center during surgery so that the surgical tool element can rotate about the pivot point without damaging the incision.

The surgical robot system of the present invention includes a gear mechanism, a base mechanism and a tool mechanism. The surgical robot system according to the present invention has no idler gears or redundant substructures. The gear mechanism includes a gear device such as a planetary bevel gear train. A planetary bevel gear train is an epicyclic gear train with bevel gears. The base mechanism is adapted to be fixedly mounted to a surface and includes a wheel device. The wheel device engages with the gear device of the gear mechanism. The tool mechanism includes a pinion device and a sleeve device. The pinion device engages with the gear device of the gear mechanism. The sleeve device is positioned at the end of the articulated linkage of the robot system. The sleeve device has a diameter to accommodate a variety of surgical tool elements.

The sleeve device engages any surgical tool element to perform various functions for the surgeon such as holding a needle, grasping a blood vessel or dissecting tissue. For example, surgical tool elements may be graspers, clamps, occluders, retractors, positioners, scissors, cutters, dilators, cameras, speculas, suction tips and tubes, needle drivers and needles, to name a few. The tool mechanism allows the surgeon to control the surgical tool element, specifically the tip of the tool element.

A controller device controls the robot system, more specifically the gear device to position and manipulate the tool mechanism including sleeve device to locate the tip of the tool element within a body cavity. The controller device is any type of power source such as one or more motors including angular or linear motors, angular or linear actuators, or a combination thereof, to monitor and affect the operational conditions of the surgical robot system. It is contemplated that the robot system may be controlled mechanically, electronically, manually, or even a combination thereof.

An input device allows a surgeon to control the controller device and may include, for example, an audio input apparatus such as a microphone, a joystick, gloves with sensors to detect finger movement, a control stick or touch screen. The input device may be wireless or integrated within the surgical robot system. In one embodiment, the input device transfers forces from the surgeon's hand or fingers to the tool element. It is contemplated that the input device provides for palpation and manipulation of tissues and tool elements. To provide responses, a tactile sensor array may be included on the sleeve device including tool element, which is coupled to a tactile sensor stimulator array on the input device, thereby reproducing the tactile sensation on the surgeon's hands. It is contemplated that the input device may include resistive/conductive, semiconductor, piezoelectric capacitive and photoelectric technologies to provide for the tactile sensation.

It is further contemplated that the robot system according to the present invention may further include an output device, or feedback device to collect, process and transmit data. Types of data may include torque, force, velocity, acceleration applied to the tool element, performance information of any mechanism or device of the surgical robot system, or any combination thereof. It is also contemplated that the output device may be integrated with one or more cameras, for example on the sleeve device or tool element, to provide a visual display of the position of the tool element within the body cavity. It is contemplated that the input device and the feedback device may be integrated as a single unit.

In one embodiment, the surgical robot system is actuated by four motors which are mounted remotely with respect to the entry point to reduce the mass and dynamic effects and increase the robot system dexterity. Each rotational degree of freedom is controlled by a motor and the fourth motor controls translation of the sleeve device of the tool mechanism. This allows a surgeon to accurately and remotely control the orientation of the tool element through the input device such as a joystick with intuitive pitch/yaw/roll motions.

The rotational motion of the sleeve device is controlled by the gear device of the gear mechanism. As mentioned above, in one embodiment the gear device is a planetary bevel gear train otherwise known as an epicyclic gear train. The translational motion of the sleeve device is controlled by a pulley arrangement in one embodiment of the present invention. In addition to a pulley arrangement, gimbals, linkages, cables, drive belts and bands, gears, optical or electromagnetic positioners are contemplated. This translation is desirable for depth positioning of the surgical tool element.

As mentioned above, the base mechanism is adapted to be fixedly mounted to a surface. Likewise, it is also contemplated that the gear mechanism or tool mechanism may be adapted to be fixedly mounted to a surface. There are numerous contemplated methods for fixedly mounting the robot system to a surface. For purposes of the present invention, any surgical holding or positioning device is contemplated for securing the robot system, for example, a spherical-jointed universal clamping device or flexible mounting arms.

The surgical robot system includes three axes: a first axis along the gear mechanism, a second axis along the base mechanism, and a third axis along the tool mechanism. The first axis, the second axis and the third axis meet at a single point, the remote center of motion ("RCM"). The motion of the surgical robot system depends on the gear device of the gear mechanism. The gear mechanism constrains the motion of the surgical tool element in the sleeve device to always pass through a fixed point in space. Thus, the RCM allows the manipulated tool element to pivot about a fixed point in space coincident with the entry point. The surgical robot system has four Degrees of Freedom ("DOF")—three rotational DOF and one translation DOF. A first degree of freedom is defined by rotation about the first axis, a second degree of freedom is defined by rotation about the second axis, a third degree of freedom is defined by rotation about the third axis and a fourth degree of freedom is defined by translation about the third axis.

A method of performing minimally invasive surgery using the robot system according to the present invention includes securing the base mechanism, which includes a first axis. A tool element is engaged within the sleeve device of the tool mechanism. The tool element is introduced into a body cavity by the tool mechanism. A gear mechanism, which includes a second axis, is rotated about the first axis. The tool mechanism, which includes a third axis, is spun about the second axis. The tool mechanism is turned about the third axis. The sleeve device is translated to position the tool element at a desired location inside the cavity, more specifically penetration depth into the cavity. These degrees of freedom allow the tool element to be positioned at a desired location inside a body cavity. For purposes of this application, the terms "rotate", "spin", "turn", "revolve" and all tenses thereof are used interchangeably herein. It should be noted that any of the four degrees of freedom may be performed alone or in any combination, as well as simultaneously.

An object of the present invention is to provide a lightweight surgical robot system designed with a compact structure that is highly dexterous and permits large orientation angles along with sufficient precision to control the position of surgical tool elements for minimally invasive surgery.

Another object of the present invention is to provide a surgical robot system fixedly mountable to a surface, such as a surgical table, such that it can "float" over a patient during surgery. The surgical robot system does not come into direct contact with the patient.

Another object of the present invention is to provide a surgical robot system that occupies minimal space within the operating room environment, for example, a space bounded by a hemisphere of radius 13.7 cm.

Another object of the present invention is to provide a surgical robot system that is compatible with existing standard equipment.

Another object of the present invention is to provide a surgical robot system with a kinematically fixed entry point that reduces or eliminates calibration time.

Another object of the present invention is to provide a surgical robot system with spherical motion to allow a surgical tool element to pivot about an entry point, thus allowing surgical access to a body cavity without a large incision.

Yet another object of the present invention is to provide a surgical robot system that reduces the "fulcrum effect". The "fulcrum effect" is known as a tool element moving in an opposite direction, e.g. right, as the surgeon's hand, e.g. left.

Yet another object of the present invention is to provide surgical robot system that is easy to control based on the linear force and displacement relations characteristic of geared mechanisms.

Yet another object of the present invention is to provide a surgical robot system that may be applicable to applications such as telesurgery.

Yet another object of the present invention is to provide effective implementation of force feedback to the surgeon allowing the surgical robot to be used in a passive mode as a kinematic data collection device such as for surgical training.

It will of course be understood that the aspects and objectives of the invention are various, and need not be all present in any given embodiment of the invention. The features, advantages and accomplishments of the invention will be further appreciated and understood upon consideration of the following detailed description of an embodiment of the invention, taken in conjunction with the drawings, in which:

DETAILED DESCRIPTION OF EMBODIMENTS OF THE INVENTION

As noted above, the invention is not limited to any particular application or use. In addition to minimally invasive surgery, uses of the present invention include, for example, open surgery, including surgery from a remote location, and microsurgery.

The structure of the surgical robot system is optimized based on kinematic analysis including forward and inverse kinematics. Forward kinematics is computation of the position and orientation of the end effector of the robot as a function of its joint angles. For purposes of this application the end effector is the sleeve device, and more specifically the tip of the tool element held by the sleeve device. Inverse kinematics is the process of determining the parameters of the surgical robot system in order to achieve a desired pose, otherwise referred to as motion planning.

Solving for the optimum surgical robot system is approached as a set of rigid mechanisms connected by joints. Varying angles of the joints yields an indefinite number of configurations. The solution to the forward kinematic problem, given these angles, is the pose or position of the surgical robot system. The solution to the inverse kinematics problem is the joint angles given the desired configuration of the end effector.

The resulting three rotational degrees of freedom ("DOF") is evaluated for the required workspace such as an operating room environment typically used in minimally invasive surgery procedures, and the fourth translational DOF is designed to satisfy all the remaining dexterity requirements such as tool element penetration depth in a patient.

By evaluating different spherical geared configurations with various link angles and pitch angles, an optimal design is achieved which performs surgical tool positioning throughout the desired kinematic workspace while occupying a small space bounded by a specific hemisphere value for the minimally invasive surgery.

Figure 1:
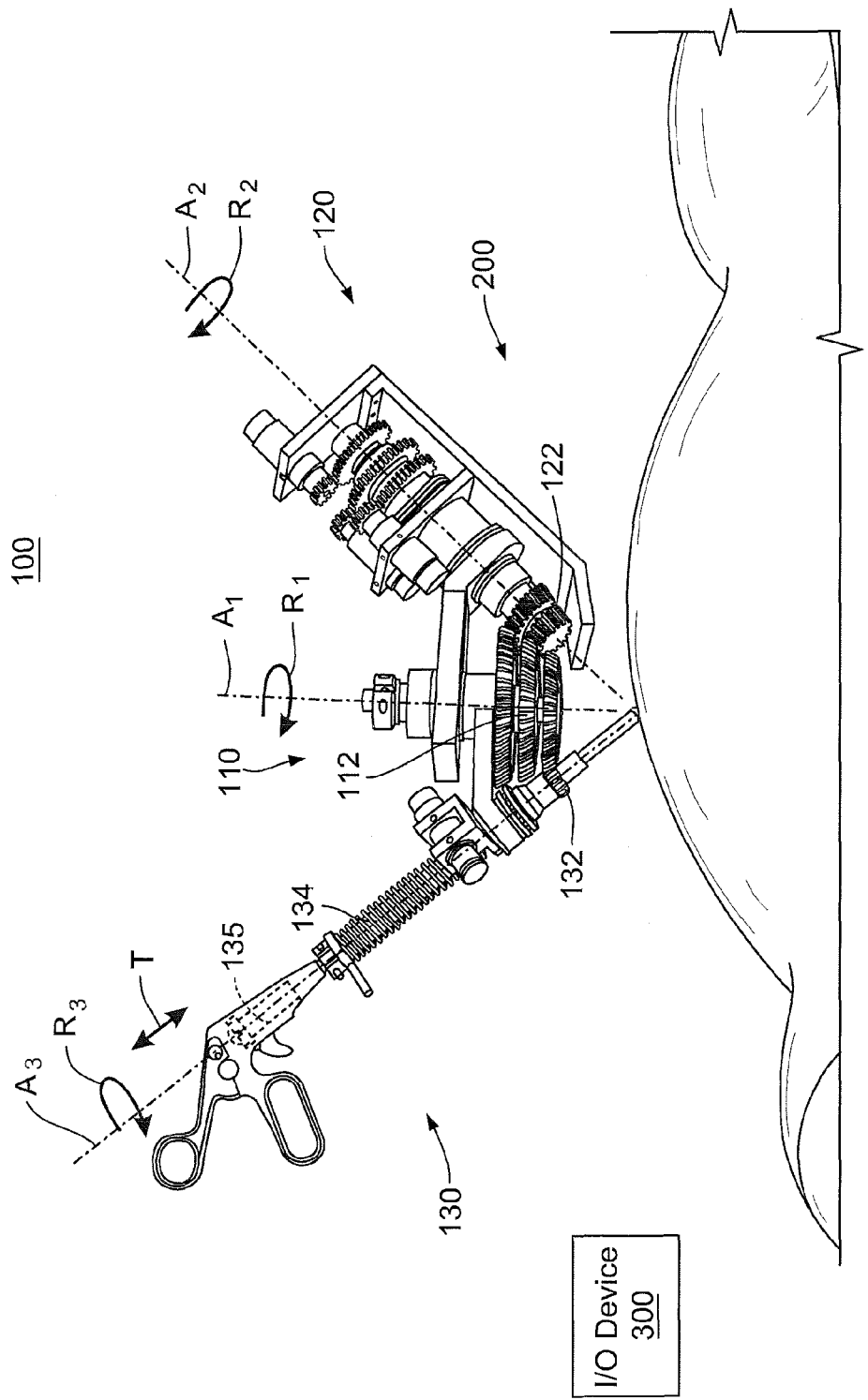
FIG. 1 illustrates an embodiment of the surgical robot system according to the present invention.

FIG. 1 shows an embodiment of the surgical robot system 100 according to the present invention. For purposes of this application, the term "spherical wrist mechanism" used herein refers to the portion of the surgical robot system 100 pertaining to the three rotational degrees of freedom only—not the translational degree of freedom. The surgical robot system 100 of the present invention includes a gear mechanism 110, a base mechanism 120 and a tool mechanism 130. The surgical robot system 100 according to the present invention has no idler gears or redundant substructures. The gear mechanism 110 includes a gear device 112 shown as a planetary bevel gear train. A planetary bevel gear train is an epicyclic gear train with bevel gears. The base mechanism 120 is adapted to be fixedly mounted to a surface and includes a wheel device 122. The wheel device 122 engages with the gear device 112 of the gear mechanism 110. The tool mechanism 130 includes a pinion device 132 and a sleeve device 134. The pinion device 132 engages with the gear device 112 of the gear mechanism 110. The sleeve device 134 is positioned at the end of the articulated linkage of the robot system 100. The sleeve device 134 has a diameter to accommodate a variety of surgical tool elements, for example, surgical tool elements with a diameter of 10 mm or less.

The sleeve device 134 holds any surgical tool element 135 to perform various functions for the surgeon such as holding a needle, grasping a blood vessel or dissecting tissue. The tool element 135 as shown in FIG. 1 is a grasper, but any tool element is contemplated, for example, clamps, occluders, retractors, positioners cutters, dilators, speculas, suction tips and tubes, needle drivers and needles. The tool mechanism 130 allows the surgeon to control the surgical tool element 135, specifically the tip of the tool element.

A controller device 200 controls the robot system 100, more specifically the gear device 112 to position and manipulate the tool mechanism 130 including sleeve device 134 to locate the tip of the tool element 135 within a body cavity. The controller device 200 comprises four motors to maneuver the surgical robot system 100—one motor each for rotation of the gear mechanism 110, base mechanism 120, tool mechanism 130 and one motor for translation of the tool mechanism 130, specifically the sleeve device 134

The input device and feedback or output device are integrated in a single unit illustrated as an I/O unit 300 in FIG. 1. The I/O unit 300 is wireless and allows a surgeon to control the controller device 200. Additionally, the I/O unit 300 provides a visual display to the surgeon of the torque, force, velocity, acceleration applied to the tool element 135 as well as the position of the tool element 135 within the body cavity.

The surgical robot system 100 includes three axes: a first axis "A1" along the gear mechanism 110, a second axis "A2" along the base mechanism 120, and a third axis "A3" along the tool mechanism 130. The first axis A1, the second axis A2 and the third axis A3 meet at a single point known as the remote center of motion ("RCM") that allows the tool element to pivot about the entry point. The surgical robot system 100 has four degrees of freedom. A first DOF is defined by rotation about the first axis A1 shown by arrow R1, a second DOF is defined by rotation about the second axis A2 shown by arrow R2, a third DOF is defined by rotation about the third axis A3 shown by arrow R3 and a fourth DOF is defined by translation about the third axis A3 shown by arrow T in FIG. 1.

A method of performing minimally invasive surgery using the robot system 100 includes securing the base mechanism 120. A tool element 135 is engaged within the sleeve device 134 of the tool mechanism 130. The tool element 135 of the sleeve device 134 is introduced into a body cavity by the tool mechanism 130. The following DOF are contemplated: the gear mechanism 110 rotated about the first axis A1, the tool mechanism 130 rotated about the second axis A2, the tool mechanism 130 rotated about the third axis A3, and the sleeve device 134 translated about the third axis A3. One or more DOF, performed alone or in any combination, position the tool element 135 at a desired location inside the cavity.

Figure 3:
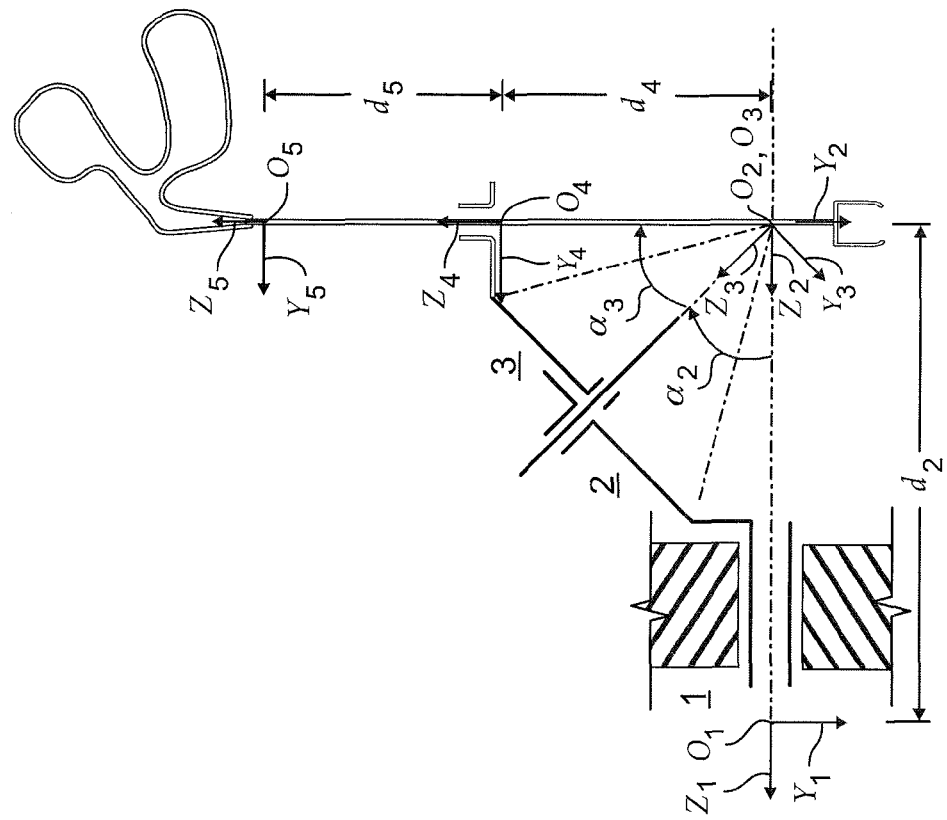
FIG. 3 illustrates an open-loop chain of the surgical robot system of FIG. 1 according to the present invention.
Figure 2:
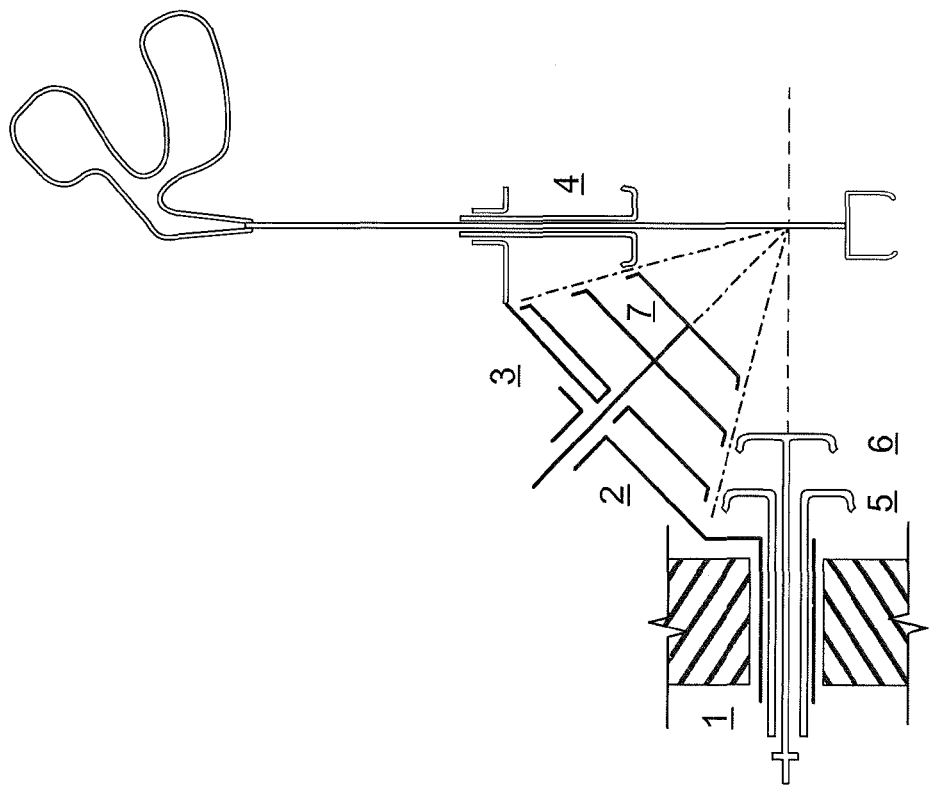
FIG. 2 illustrates a schematic of the surgical robot system embodiment of FIG. 1 according to the present invention.

The surgical robot system according to the present invention is composed of seven links joined by three gear pairs and six turning pairs. FIG. 2 shows a schematic of the surgical robot system embodiment of FIG. 1 and FIG. 3 shows an open-loop chain of the surgical robot system of FIG. 1 according to the present invention. The turning pairs are arranged such that an open space is maintained at the center of the surgical robot system—where the surgical tool element enters the patient. As shown in FIG. 3, the open-loop chain consists of links and turning pairs only, and the relative rotation between every pair of adjacent links in the equivalent open-loop chain can be derived from a set of fundamental circuit equations and coaxial conditions. The link angles between turning pairs are set at values no more than 90° to provide a larger, open center space to avoid self-collisions within the surgical robot system during surgeries.

FIG. 2 and FIG. 3 illustrate the assignment of frames, joints and links of the surgical robot system in the zero position. As shown, $\theta_{21}$, $\theta_{51}$, and $\theta_{61}$ are the input angles, while *$\theta_{21}$, $\theta_{32}$, and $\theta_{43}$ are the joint angles or the unknown variables needed for the analysis of the equivalent open-loop chain, where *$\theta\theta_{21} = \theta_{21}$. The link angle $\alpha_{j+1}$ expresses the angle between the $i^{th}$ and $(i+1)^{st}$ axes. When *$\theta_{21} = 0$, link 2 lies in a plane perpendicular to the plane created by $Z_1$ and $X_1$. When $\theta_{32} = 0$, link 3 is unfolded in the plane created by $Z_2$ and $Y_2$. Using the Denavit-Hartenberg ("DH") convention of Craig, the DH parameters for the mechanism are summarized below in Table 1:

TABLE 1

| i | $\alpha_{i-1}$ | $a_{i-1}$ | $d_i$ | $\theta_i$ |
|---|---|---|---|---|
| 2 | 0 | 0 | $-d_2$ | *$\theta_{21}$ |
| 3 | $\alpha_2$ | 0 | 0 | $\theta_{32}$ |
| 4 | $\alpha_3$ | 0 | $+d_4$ | $\theta_{43}$ |
| 5 | 0 | 0 | $+d_5$ | 0 |

The orientation of the tip of the surgical tool element is controlled by the cooperative motions of the three coaxial input angles. Thus, kinematic analysis of the surgical robot system is a process of determining the relationship between the three input angles and the coordinates of the end effector.

For the coordinate systems shown in FIG. 2 and FIG. 3, there are three fundamental circuits (f-circuits) which describe the kinematic loops in the mechanism. The fundamental circuit equations are as follows:

$$f\text{-circuit } (5, 3)(2): \theta_{32} = N_{53}\theta_{52} \tag{1}$$

$$f\text{-circuit } (6, 7)(2): \theta_{72} = N_{67}\theta_{62} \tag{2}$$

$$f\text{-circuit } (7, 4)(3): \theta_{43} = N_{74}\theta_{73} \tag{3}$$

where (i, j)(k) represents a gear mesh between links i and j, with link k as the carrier, and $N_{ij}$ is the gear ratio as determined by numbers of teeth. The coaxial conditions are:

$$\theta_{52} = \theta_{51} - \theta_{21} \tag{4}$$

$$\theta_{62} = \theta_{61} - \theta_{21} \tag{5}$$

$$\theta_{73} = \theta_{72} - \theta_{32} \tag{6}$$

So a set of six linear equations are achieved. To solve these equations for the forward kinematics, all the other variables except the input angles and the joint angles from Equations (1) through (6) above need to be eliminated.

Substituting Equation (4) into Equation (1) yields:

$$\theta_{32} = N_{53}(\theta_{51} - \theta_{21}) \tag{7}$$

Substituting Equation (5) into Equation (2) yields:

$$\theta_{72} = N_{67}(\theta_{61} - \theta_{21}) \tag{8}$$

Substituting Equation (7) and Equation (8) into (Equation 6) yields:

$$\theta_{73} = [N_{67}(\theta_{61} - \theta_{21})] - [N_{53}(\theta_{51} - \theta_{21})] \quad (9)$$

Substituting Equation (9) into Equation (3) yields $$\theta_{43} = N_{74}\{[N_{67}(\theta_{61} - \theta_{21})] - [N_{53}(\theta_{51} - \theta_{21})]\} \quad (10)$$

where the gear ratios are $N_{53} = -T_5/T_3$, $N_{67} = -T_6/T_7$, and $N_{74} = T_7/T_4$.

The orientation of the end effector is represented by the fifth coordinate system as measured in the ground Equation (1) reference frame. Therefore, a set of three vectors ($^1X_5$, $^1Y_5$, $^1Z_5$) can be used to derive a 3×3 transformation matrix representing the orientation of the surgical tool in terms of the base frame 1:

$$^1X_5 = \begin{bmatrix} ^1_5 X_x \\ ^1_5 X_y \\ ^1_5 X_z \end{bmatrix} = {}^1_5R \begin{bmatrix} 1 \\ 0 \\ 0 \end{bmatrix} = {}^1_2R * {}^2_3R * {}^3_4R * {}^4_5R * \begin{bmatrix} 1 \\ 0 \\ 0 \end{bmatrix} \quad (11a)$$

-continued $$^1Y_5 = \begin{bmatrix} ^1_5 Y_x \\ ^1_5 Y_y \\ ^1_5 Y_z \end{bmatrix} = {}^1_5R \begin{bmatrix} 0 \\ 1 \\ 0 \end{bmatrix} = {}^1_2R * {}^2_3R * {}^3_4R * {}^4_5R * \begin{bmatrix} 0 \\ 1 \\ 0 \end{bmatrix} \quad (11b)$$

$$^1Z_5 = \begin{bmatrix} ^1_5 Z_x \\ ^1_5 Z_y \\ ^1_5 Z_z \end{bmatrix} = {}^1_5R \begin{bmatrix} 0 \\ 0 \\ 1 \end{bmatrix} = {}^1_2R * {}^2_3R * {}^3_4R * {}^4_5R * \begin{bmatrix} 0 \\ 0 \\ 1 \end{bmatrix} \quad (11c)$$

where, as an example of the notation, $^1_5 x_y$ denotes the y-component of the vector $X_5$ as measured in frame 1, and $${}^1_2R = \begin{bmatrix} c\theta_{21} & -s\theta_{21} & 0 \\ s\theta_{21} & c\theta_{21} & 0 \\ 0 & 0 & 1 \end{bmatrix} \quad (12a)$$

$${}^2_3R = \begin{bmatrix} c\theta_{32} & -s\theta_{32} & 0 \\ s\theta_{32}c\alpha_2 & c\theta_{32}c\alpha_2 & -s\alpha_2 \\ s\theta_{32}s\alpha_2 & c\theta_{32}s\alpha_2 & c\alpha_2 \end{bmatrix} \quad (12b)$$

$${}^3_4R = \begin{bmatrix} c\theta_{43} & -s\theta_{43} & 0 \\ s\theta_{43}c\alpha_3 & c\theta_{43}c\alpha_3 & -s\alpha_3 \\ s\theta_{43}s\alpha_3 & c\theta_{43}s\alpha_3 & c\alpha_3 \end{bmatrix} \quad (12c)$$

-continued $${}^4_5R = \begin{bmatrix} 1 & 0 & 0 \\ 0 & 1 & 0 \\ 0 & 0 & 1 \end{bmatrix} \quad (12d)$$

Substituting Equation (12) into Equation (11c) and expanding the matrix product yields:

$$^1Z_5 = \begin{bmatrix} ^1_5 Z_x \\ ^1_5 Z_y \\ ^1_5 Z_z \end{bmatrix} \quad (13)$$

$$= \begin{bmatrix} -(-c\theta_{21}s\theta_{32} - s\theta_{21}c\theta_{32}c\alpha_2)s\alpha_3 + s\theta_{21}c\alpha_3 s\alpha_2 \\ -(-s\theta_{21}s\theta_{32} + c\theta_{21}c\theta_{32}c\alpha_2)s\alpha_3 - c\theta_{21}c\alpha_3 s\alpha_2 \\ -c\theta_{32}s\alpha_3 s\alpha_2 + c\alpha_3 c\alpha_2 \end{bmatrix}$$

Substituting Equation (7) into Equation (13), the forward kinematics of the vector $^1Z_5$ expressed by the input angles and mechanism parameters can be defined as:

$$^1Z_5 = \begin{bmatrix} -\{-c\theta_{21}s[N_{53}(\theta_{51} - \theta_{21})] - s\theta_{21}c[N_{53}(\theta_{51} - \theta_{21})]c\alpha_2\}s\alpha_3 + s\theta_{21}c\alpha_3 s\alpha_2 \\ -\{-s\theta_{21}s[N_{53}(\theta_{51} - \theta_{21})] + c\theta_{21}c[N_{53}(\theta_{51} - \theta_{21})]c\alpha_2\}s\alpha_3 - c\theta_{21}c\alpha_3 s\alpha_2 \\ -c[N_{53}(\theta_{51} - \theta_{21})]s\alpha_3 s\alpha_2 + c\alpha_3 c\alpha_2 \end{bmatrix} \quad (14)$$

Equation (13) and Equation (14) demonstrate that the Z-axis of the end effector is independent of the joint angle $\theta_{43}$, which is controlled by the inputs $\theta_{21}$, $\theta_{51}$ and $\theta_{61}$ according to Equation (10). Also, it was found that the input angle $\theta_{61}$ influences $\theta_{43}$ but not $*\theta_{21}$ or $\theta_{32}$. On the other hand, $\theta_{61}$ has no contribution to the orientation of the rotation axis of the end effector, or sleeve device; rather, it controls the rotation of the end effector about its own axis. This decoupling of one of the three DOF is a positive outcome in the sense of simplified kinematics.

Given the link angles, $\theta_2$ and $\theta_3$, and the orientation of the rotation axis of the surgical tool in terms of frame 1, the joint angles $\theta_{43}$, $\theta_{32}$, and $*\theta_{21}$ of the robot, which orient the tool to the desired position, can be calculated. Using the joint angles $\theta_{43}$, $\theta_{32}$, and $*\theta_{21}$ and the gear ratios between the gear pairs, the input angles can be determined as shown in Table 3:

TABLE 3

| End effector position/orientation | | Joint angles | | Input angles |
|---|---|---|---|---|
| $\begin{bmatrix} ^1X_5 \\ ^1Y_5 \\ ^1Z_5 \end{bmatrix}$ | $\Rightarrow$ | $\begin{bmatrix} *\theta_{21} \\ \theta_{32} \\ \theta_{43} \end{bmatrix}$ | $\Rightarrow$ | $\begin{bmatrix} \theta_{21} \\ \theta_{51} \\ \theta_{61} \end{bmatrix}$ |

Using the third element (z-component) of the vector $^1Z_5$, $\cos\theta_{32}$ from Equation (13) can be expressed as:

$$c\theta_{32} = \frac{c\alpha_3 c\alpha_2 - \frac{1}{5}Z_z}{s\alpha_3 s\alpha_2} \quad (15)$$

Therefore, two possible solutions for $\theta_{32}$ are as follows using the trigonometric identities:

$$\theta_{32} = \tan^{-1}\frac{\pm\sqrt{1-\left(\frac{c\alpha_3 c\alpha_2 - \frac{1}{5}Z_z}{c\alpha_3 c\alpha_2}\right)^2}}{\frac{c\alpha_3 c\alpha_2 - \frac{1}{5}Z_z}{c\alpha_3 c\alpha_2}}$$

$$= \tan^{-1}\frac{\pm\sqrt{s^2\alpha_3 s^2\alpha_2 - (c\alpha_3 c\alpha_2 - \frac{1}{5}Z_z)^2}}{c\alpha_3 c\alpha_2 - \frac{1}{5}Z_z} \quad (16)$$

Both solutions of $\theta_{32}$ are accessible for any reachable $^1Z_5$ in the workspace; however, to achieve smooth robot motions assuming closely spaced kinematic setpoints, the value of $\theta_{32}$ is chosen to be "the closest solution" to the previous position of the end effector.

Using the first and second elements (x- and y-components) of the vector $^1Z_5$ in Equation (13) to solve for $\sin\theta_{21}$ and $\cos\theta_{21}$ gives:

$$c\theta_{21} = \frac{\frac{1}{5}Z_x s\theta_{32} s\alpha_3 - \frac{1}{5}Z_y(c\theta_{32}c\alpha_2 s\alpha_3 + c\alpha_3 s\alpha_2)}{(c\theta_{32}c\alpha_2 s\alpha_3 + c\alpha_3 s\alpha_2)^2 + s^2\theta_{32}s^2\alpha_3} \quad (17)$$

$$s\theta_{21} = \frac{\frac{1}{5}Z_x(c\theta_{32}c\alpha_2 s\alpha_3 + c\alpha_3 s\alpha_2) + \frac{1}{5}Z_y s\theta_{32} s\alpha_3}{(c\theta_{32}c\alpha_2 s\alpha_3 + c\alpha_3 s\alpha_2)^2 + s^2\theta_{32}s^2\alpha_3} \quad (18)$$

Thus, $\theta_{21}$ is $$\theta_{21} = \tan^{-1}\frac{\frac{1}{5}Z_x(c\theta_{32}c\alpha_2 s\alpha_3 + c\alpha_3 s\alpha_2) + \frac{1}{5}Z_y s\theta_{32} s\alpha_3}{\frac{1}{5}Z_x s\theta_{32} s\alpha_3 - \frac{1}{5}Z_y(c\theta_{32}c\alpha_2 s\alpha_3 + c\alpha_3 s\alpha_2)} \quad (19)$$

where the value of $\theta_{32}$ from Equation (16) is not substituted in Equation (19) only for brevity and clarity.

Similar to Equation (13), the vector $^1X_5$ and $^1Y_5$ can be expressed as Equation (20) and Equation (21).

Using the first and second elements (x- and y-components) of the vector $^1X_5$ in Equation (20) and the previous results, $\sin\theta_{43}$ and $\cos\theta_{43}$ can be solved by Equation (22) and Equation (23).

$$^1X_5 = \begin{bmatrix} \frac{1}{5}X_x \\ \frac{1}{5}X_y \\ \frac{1}{5}X_z \end{bmatrix}$$

$$= \begin{bmatrix} (c\theta_{21}c\theta_{32} - s\theta_{21}s\theta_{32}c\alpha_2)c\theta_{43} + (-c\theta_{21}s\theta_{32} - s\theta_{21}c\theta_{32}c\alpha_2)s\theta_{43}c\alpha_3 + s\theta_{21}s\theta_{43}s\alpha_2 s\alpha_3 \\ (s\theta_{21}c\theta_{32} + c\theta_{21}s\theta_{32}c\alpha_2)c\theta_{43} + (-s\theta_{21}s\theta_{32} + c\theta_{21}c\theta_{32}c\alpha_2)s\theta_{43}c\alpha_3 - c\theta_{21}s\theta_{43}s\alpha_2 s\alpha_3 \\ s\theta_{32}s\alpha_2 c\theta_{43} + c\theta_{32}s\alpha_2 s\theta_{43}c\alpha_3 + c\alpha_2 s\theta_{43}s\alpha_3 \end{bmatrix} \quad (20)$$

$$^1Y_5 = \begin{bmatrix} \frac{1}{5}Y_x \\ \frac{1}{5}Y_y \\ \frac{1}{5}Y_z \end{bmatrix}$$

$$= \begin{bmatrix} -(c\theta_{21}c\theta_{32} - s\theta_{21}s\theta_{32}c\alpha_2)s\theta_{43} + (-c\theta_{21}s\theta_{32} - s\theta_{21}c\theta_{32}c\alpha_2)c\theta_{43}c\alpha_3 + s\theta_{21}c\theta_{43}s\alpha_2 s\alpha_3 \\ -(s\theta_{21}c\theta_{32} + c\theta_{21}s\theta_{32}c\alpha_2)c\theta_{43} + (-s\theta_{21}s\theta_{32} + c\theta_{21}c\theta_{32}c\alpha_2)c\theta_{43}c\alpha_3 - c\theta_{21}c\theta_{43}s\alpha_2 s\alpha_3 \\ -s\theta_{32}s\alpha_2 s\theta_{43} + c\theta_{32}s\alpha_2 c\theta_{43}c\alpha_3 + c\alpha_2 c\theta_{43}s\alpha_3 \end{bmatrix} \quad (21)$$

$$s\theta_{43} = \frac{\frac{1}{5}X_y(c\theta_{32}c\theta_{21} - s\theta_{32}s\theta_{21}c\alpha_2) - \frac{1}{5}X_x(c\theta_{32}s\theta_{21} + s\theta_{21} + s\theta_{32}c\theta_{21}c\alpha_2)}{-c\theta_{32}s\alpha_2 s\alpha_3 + c\alpha_3 c\alpha_2} \quad (22)$$

$$c\theta_{43} = \frac{\frac{1}{5}X_x(c\theta_{32}c\theta_{21}c\alpha_2 c\alpha_s - s\theta_{32}s\theta_{21}c\alpha_3 - c\theta_{21}s\alpha_2 s\alpha_3) -}{\frac{1}{5}X_y(-c\theta_{32}s\theta_{21}c\alpha_2 c\alpha_s - s\theta_{32}c\theta_{21}c\alpha_3 + s\theta_{21}s\alpha_2 s\alpha_3)} \quad (23)$$

Similar to Equation (19), $$\theta_{43} = \tan^{-1}\frac{\frac{1}{5}X_y(c\theta_{32}c\theta_{21} - s\theta_{32}s\theta_{21}c\alpha_2) -}{\frac{1}{5}X_x(c\theta_{32}s\theta_{21} + s\theta_{32}c\theta_{21}c\alpha s\alpha_3)}{\frac{1}{5}X_x(c\theta_{32}c\theta_{21}c\alpha_2 c\alpha_s - s\theta_{32}s\theta_{21}c\alpha_3 - c\theta_{21}s\alpha_2 s\alpha_3) -}{\frac{1}{5}X_y(-c\theta_{32}s\theta_{21}c\alpha_2 c\alpha_s - s\theta_{32}c\theta_{21}c\alpha_3 + s\theta_{21}s\alpha_2 s\alpha_3)} \quad (24)$$

The denominator of Equation (22) and Equation (23) was cancelled in Equation (24). If the denominator of Equation (22) is positive, Equation (24) gives a correct result of $\theta_{43}$; otherwise, 180° is added to $\theta_{43}$ to achieve the correct result.

Using the three joint angles above and the gear ratios between the gear pairs, the input angles can then be determined. By Equation (7), the solution of $\theta_{51}$ results in $$\theta_{51} = \frac{\theta_{32}}{N_{53}} + \theta_{21} \quad (25)$$

Solving Equation (10) for $\theta_{61}$ using Equation (21) and Equation (22), and using the value of $\theta_{43}$ from Equation (24), $$\theta_{61} = \theta_{21} + N_{76}\theta_{32} + N_{76}N_{47}\theta_{43} \quad (26)$$

By substituting and rearranging, using fundamental circuit equations and coaxial conditions, we can get the relations between input angles and joint angles.

$$\begin{bmatrix} \theta_{21} \\ \theta_{51} \\ \theta_{61} \end{bmatrix} = \begin{bmatrix} 1 & 0 & 0 \\ 1 & N_{35} & 0 \\ 1 & N_{76} & N_{76}N_{47} \end{bmatrix} \begin{bmatrix} *\theta_{21} \\ \theta_{32} \\ \theta_{43} \end{bmatrix} \quad (27)$$

Ninety-five percent of minimally invasive surgery surgical tool motions are contained by a cone having a vertex angle of 60° with its tip located at the minimally invasive surgery port, known as a target workspace defined as the dexterous workspace. The workspace of the spatial spherical wrist mechanism based on the kinematic analysis above is a sector of a spherical shell, and the center angle of this sector includes the cone vertex angle of the dexterous workspace. However, the above kinematic analysis does not consider mechanism design constraints. In fact, only a partial area on this spherical surface can be used as the reachable workspace of the spherical wrist mechanism due to self-collisions between links. During the design process, it was found that link angles directly affect the center angle of the sector. Even with consistent link angles a, different pitch angles of the bevel-gears—the angle between the pitch surface and the rotation axis—led to variations in the portions of the theoretical workspace made infeasible due to internal interference. Moreover, link angles and pitch angles cooperatively restricted the motion range of the joint angles, which controlled the orientation of the end effector. As a result, the shape and the size of the available workspace are determined by the link angles ($\alpha_2$, $\alpha_3$), pitch angles ($\beta_3$, $\beta_4$, $\beta_5$, $\beta_6$, $\beta_7$), and the physical size or scale of the bevel-gear train.

Thus, to design a compact, lightweight surgical robot system with high dexterity yet permitting large enough orientation angles to reach the full extent of the abdomen for minimally invasive surgery procedures, the optimization process focuses on defining the mechanism parameters such as link angles and pitch angles. By considering these mechanism parameters as optimization variables and adding physical configuration limitations such as the range of joint angles into the optimization, an effective mechanism device with the fully reachable dexterous workspace can be obtained.

To simplify the optimization process, equal values of $\alpha_2$ and $\alpha_3$ are assumed as well as equal pitch angles for coaxial bevel-gears. From characteristics derived from these special situations, the general optimization approach of the mechanism configuration can be obtained.

Figure 4:
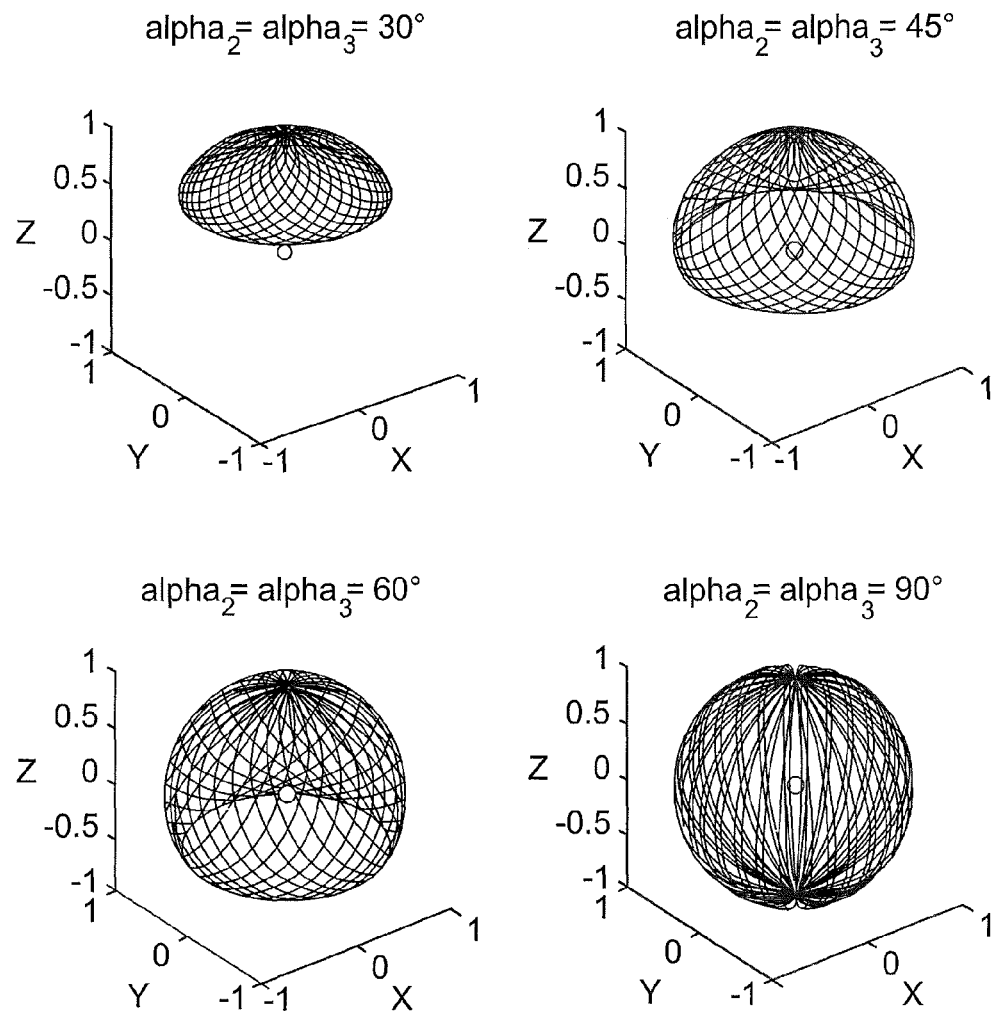
FIG. 4 illustrates the theoretical workspace of the surgical robot system with different link angles according to the present invention.

Given the values of the link angles ($\alpha_2$, $\alpha_3$), the sector of the sphere is defined as the theoretical workspace without considering practical self-collisions between links. FIG. 4 shows the theoretical workspace of the surgical robot system with different link angles of 30°, 45°, 60°, and 90°. As shown in FIG. 4, the black point is the center of the surgical robot system, or the minimally invasive surgery entry point. The center angle of the sector is ideally the sum of link angles $\alpha_2$ and $\alpha_3$, which means that a design with larger link angles will have a larger workspace. However, the link angle can not be unrestrictedly large. If the sector center angle is larger than 180°, the surgical robot system will not provide enough open space to allow the tool to be inserted into the patient, and also it may lead to collisions with the surgical tool itself as it is inserted through the sleeve device. Moreover, to avoid robot-patient collisions, the sum of $\alpha_2$ and $\alpha_3$ should be kept less than 90°—the patient is conservatively modeled as a planar workspace boundary passing through the RCM. Meanwhile, the sum of $\alpha_2$ and $\alpha_3$ must be larger than 60° to make sure the surgical tool can access the target anatomy. Thus, the optimal mechanism design has link angles a in the range of 30° to 45°, and the value is chosen as small as possible to obtain the most compact surgical robot system configuration while meeting the constraints of the workspace.

Figure 5:
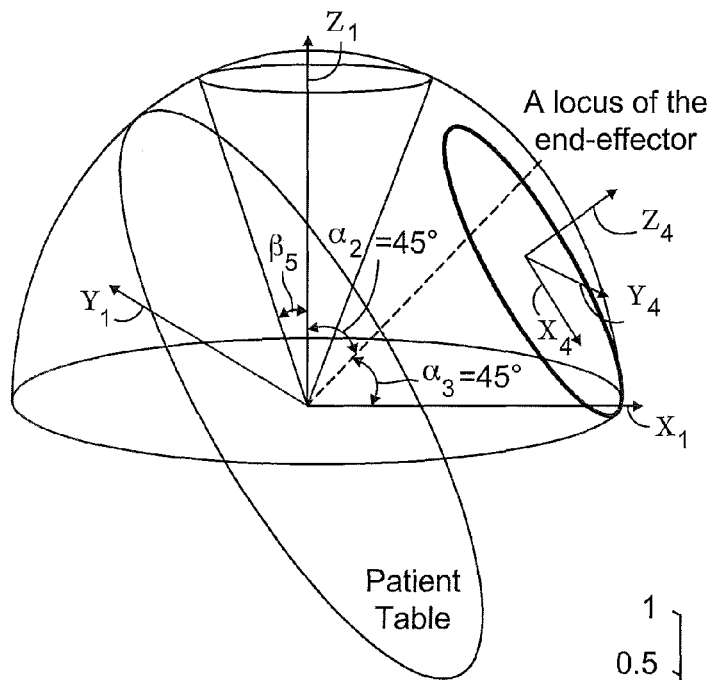
FIG. 5 illustrates the coordinate systems of various frames of the end effector orientation according to the present invention.

Considering the physical mechanism configuration, the pitch angle of gear 5 ($\beta_5$) creates a right circular cone with a vertex angle of $2\beta_5$ located at the center of the sphere as shown in FIG. 5. FIG. 5 is an illustration of the coordinate systems of frame 1 and frame 4 end effector orientation according to the present invention. The surgical tool cannot reach the intersection area between this cone and the theoretical sphere. Take the case of $\alpha_2=\alpha_3=45°$ as an example; the usable range of the sector reduces to ($\alpha_2+\alpha_3-\beta_5$), which demonstrates that a smaller pitch angle of gear 5 with constant link angles will present a better reachable workspace.

Another main surgical robot system limitation is the self-collision between gear 4 and gears 5 or 6, which further constrains the true reachable workspace of the system. The degree of limitation depends on the pitch angle and the diameter of gear 4, with lower values of the pitch angle and the diameter resulting in a smaller interference space and a larger available workspace.

Table 2 compares the practical workspaces of different candidate designs with the same theoretical workspace, but various pitch angles. With the same theoretical workspace of 90°, minimizing the pitch angles of gears 4, 5, and 6 and maximizing the pitch angles of gears 3 and 7 will effectively reduce the interference space and augment the reachable workspace of the mechanism.

TABLE 2

| Design | $\beta_5/\beta_6$ | $\beta_3/\beta_7$ | $\beta_4$ | $\alpha_2$ | $\alpha_3$ | Theoretical Workspace | Practical Workspace | Collision Point |
|---|---|---|---|---|---|---|---|---|
| 1 | 30° | 15° | 30° | 45° | 45° | 90° | 47° | Links 5 and 4 |
| 2 | 22.5° | 22.5° | 22.5° | 45° | 45° | 90° | 53° | Links 6 and 4 |
| 3 | 15° | 30° | 15° | 45° | 45° | 90° | 68° | Links 5 and 4 |
| 4 | 10° | 35° | 10° | 45° | 45° | 90° | 75° | Links 6 and 4 |

Figure 6:
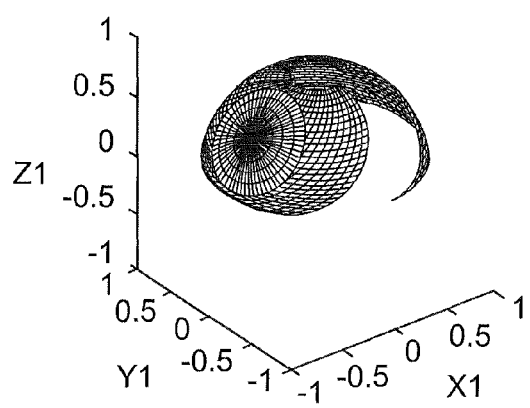
FIG. 6 illustrates a workspace plot for $\alpha_2=\alpha_3=40°$ according to the present invention.

Based on preliminary kinematic optimization results, an optimal system design of $\alpha_2=\alpha_3=40°$ and $\beta_4=\beta_5=\beta_6=10°$, $\beta_3=\beta_7=30°$ with a characteristic dimension of a sphere radius of 13.7 cm (see FIG. 1) was chosen. The range of motion for the first joint angle is $0°<*\theta_{21}<300°$ and the range of motion for the second joint angle is $0°<\theta_{32}<156°$. FIG. 6 is an illustration of a workspace plot for $\alpha_2=\alpha_3=40°$ outlining the true reachable workspace of the optimal design with the dexterous workspace included. This mechanism provides a sufficient reachable workspace with the true center angle being 65°, and self-collision occurs (bounding this workspace) between links 4 and 6. The workspace plot of FIG. 6 shows the reachable workspace with the center angle of 65° in gray, and the dexterous workspace with the cone vertex angle of 60° in black.

Figure 7:
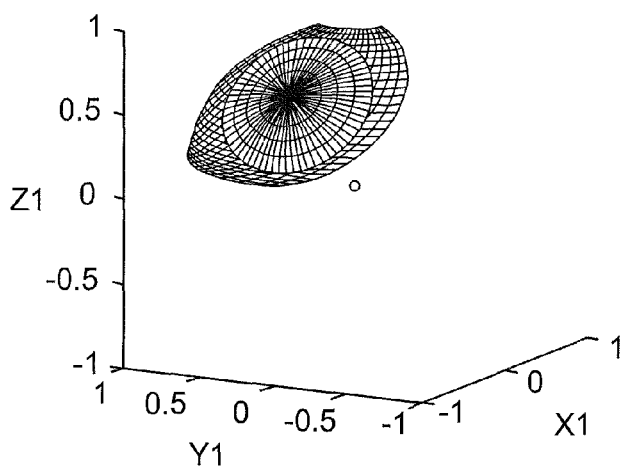
FIG. 7 illustrates a workspace plot for $\alpha_2=\alpha_3=40°$ with the motion range of $*\theta_{21}$ being 115° according to the present invention.

For this surgical robot system to reach the dexterous workspace required in surgery, the joint angle $\theta_{32}$ has to rotate from 0° to 165° to cover the center angle of 65°; however, the joint angle $*\theta_{21}$ only needs to move in the range of 115° rather than the whole range of 300°. FIG. 7 shows the workspace plot for $\alpha_2 = \alpha_3 = 40°$ with the motion range of $*\theta_{21}$ being 115° and the motion range of $\theta_{32}$ being 165°. This practical workspace still contains the dexterous workspace in it while requiring less joint motion of $*\theta_{21}$. This result demonstrates that the optimal design also has the ability to reach the extended dexterous workspace which is defined as an elliptical cone with principal vertex angles of 60° and 90° such that minimally invasive surgery tools can reach any organ in the abdomen. This is done by increasing the motion range of $*\theta_{21}$ from 115° to 137°. The workspace plot of FIG. 7 shows the reachable workspace with the center angle of 65° in gray and with the dexterous workspace in black included.

Essentially, the dexterous workspace really only concerns two of the rotational DOF. The rotation of the tool about its axis and the translation along the same axis can be considered separately. In this case, the tool-axis rotation has an unrestricted range. The insertion depth of the surgical tool element past the entry point, which represents the range of translation displacement for the fourth DOF, is 168 mm assuming a standard laparoscopic tool element shaft of 310 mm. This insertion depth is mainly influenced by the compressed length of the sleeve device. If greater penetration depth is desired, laparoscopic tool elements with longer shafts are available, or custom tool elements could be designed. Actuation of the tool element tip can be achieved by mounting an actuator to a standard laparoscopic tool element or by using a custom-designed tool element with an integrated actuator.

The main advantages of the surgical robot system over other existing surgical robotic systems is that the robot is much smaller, is lightweight, and has a limited space envelope throughout its workspace, so it is safer and easier to integrate in an operating room environment than larger robotic system. This compact, high dexterity system may be used in conjunction with a three-DOF robotic arm such as a gross positioning mechanism for telesurgery.

While the present invention has been described with reference to particular embodiments, those skilled in the art will recognize that many changes may be made thereto without departing from the scope of the present invention. Each of these embodiments and variants thereof is contemplated as falling with the scope of the claimed invention, as set forth in the following claims.

What is claimed is:

1. A surgical robot system, comprising:
    a gear mechanism including a gear device and a first axis along said gear mechanism;
    a base mechanism including a wheel device and a second axis along said base mechanism;
    a tool mechanism including a sleeve device, a pinion device and a third axis along said tool mechanism, wherein said sleeve device is adaptable to hold a surgical tool element, wherein the first axis, the second axis, and the third axis meet at a single point;
    said wheel device is secured to said gear device and said pinion device is secured to said gear device such that the system includes a first degree of freedom defined by rotation about said first axis, a second degree of freedom defined by rotation about said second axis, a third degree of freedom defined by rotation about said third axis and a fourth degree of freedom defined by translation about said third axis;
    a controller device; and
    an input device to affect said controller device in order to operate the surgical robot system.

2. The surgical robot system of claim 1, wherein said base mechanism is adapted to be fixedly mounted to a surface.

3. The surgical robot system of claim 1, wherein said controller device is coupled to said base mechanism for rotating said gear mechanism and said tool mechanism about said first axis.

4. The surgical robot system of claim 1, wherein said controller device is coupled to said gear mechanism for rotating said tool mechanism about said second axis.

5. The surgical robot system of claim 1, wherein said controller device is coupled to said tool mechanism for rotating said tool mechanism about said third axis.

6. The surgical robot system of claim 1, wherein said controller device is coupled to said tool mechanism for translating said tool mechanism about said third axis.

7. A method of performing minimally invasive surgery using a robot system, comprising the steps of:
    securing a base mechanism wherein a first axis is along the base mechanism;
    engaging a tool element within a sleeve device of a tool mechanism;
    introducing the tool element into a body cavity;
    rotating a gear mechanism about the first axis to position the tool element at a desired location inside the cavity, wherein a second axis is along the gear mechanism;
    spinning the tool mechanism about the second axis to position the tool element at a desired location inside the cavity, wherein a third axis is along the tool mechanism;
    turning the tool mechanism about the third axis to position the tool element at a desired location inside the cavity; and
    translating the tool mechanism to position the tool element at a desired location inside the cavity, wherein the first axis, the second axis, and the third axis meet at a single point.

8. The method of performing minimally invasive surgery using a robot system of claim 7, wherein said rotating step, said spinning step, and said turning step are performed simultaneously.

9. A surgical robot system for minimally invasive surgery, comprising:
    a base mechanism adapted to be fixedly mounted to a surface;
    a gear mechanism including a planetary bevel gear train, wherein said gear mechanism is rotatably mounted to said base mechanism for rotation about a first axis along said base mechanism;
    a tool mechanism including a sleeve device holding a surgical tool element, wherein said tool mechanism is rotatably mounted to said gear mechanism for rotation about a second axis along said gear mechanism;
    said tool mechanism further translatable and rotatable about a third axis along said tool mechanism;
    a controller device for controlling said gear mechanism and said tool mechanism; and
    an input device to operate said controller device to position and manipulate said surgical tool element within a body cavity, wherein the first axis, the second axis, and the third axis meet at a single point.

10. The surgical robot system of claim 9 further comprising a feedback device to collect, process and transmit data applied to said surgical tool element.

11. The surgical robot system of claim 10, wherein said feedback device and said input device are integrated as a single unit.

* * * * *